United States Patent [19]

Relles et al.

[11] 4,054,577

[45] Oct. 18, 1977

[54] PREPARATION OF AROMATIC BISIMIDES

[75] Inventors: Howard M. Relles, Rexford; Donald S. Johnson, Scotia, both of N.Y.

[73] Assignee: General Electric Company, Schenectady, N.Y.

[21] Appl. No.: 683,648

[22] Filed: May 6, 1976

[51] Int. Cl.$^2$ ............................................. C07D 209/34
[52] U.S. Cl. ............................ 260/326 N; 260/47 CP; 260/326 A; 260/326 S; 260/343.3 R; 260/515 P; 260/519; 252/511
[58] Field of Search ...................................... 260/326 N

[56] References Cited

U.S. PATENT DOCUMENTS 3,140,322  7/1964  Frildte et al. .................... 252/455 Z
3,879,428  4/1975  Heath et al. ................. 260/326 N X

OTHER PUBLICATIONS

Keough et al., Journ. Amer. Chem. Soc, 83, pp. 3536–3537.

*Primary Examiner*—Ethel G. Love
*Attorney, Agent, or Firm*—Joseph T. Cohen; Jerome C. Squillaro

[57] ABSTRACT

Aromatic bisimides can be prepared by effecting reaction under anhydrous conditions between a 3- or 4-nitro-N-substituted phthalimide with an aromatic dihydroxy compound in the presence of a certain class of dipolar aprotic compounds as solvent and solid potassium carbonate and in the further presence of a particulate zeolite adsorbent.

11 Claims, No Drawings

PREPARATION OF AROMATIC BISIMIDES

This invention relates to the preparation of aromatic bisimides by the process of effecting reaction between a 3- or 4-nitro-N-substituted phthalimide with an aromatic dihydroxy compound in the presence of potassium carbonate and a zeolite, using a specific class of dipolar aprotic compounds as a solvent.

More particularly, the invention is concerned with a process for making aromatic bisimides of the general formula

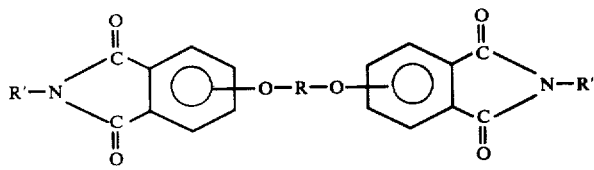

which process comprises simultaneously effecting reaction under substantially anhydrous conditions in the presence of potassium carbonate between a nitro-N-substituted phthalimide of the general formula

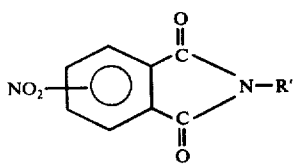          II with an aromatic dihydroxy compound of the general formula

         III

HO — R — OH where R is a member selected from the class consisting of
a. divalent radicals of the formula

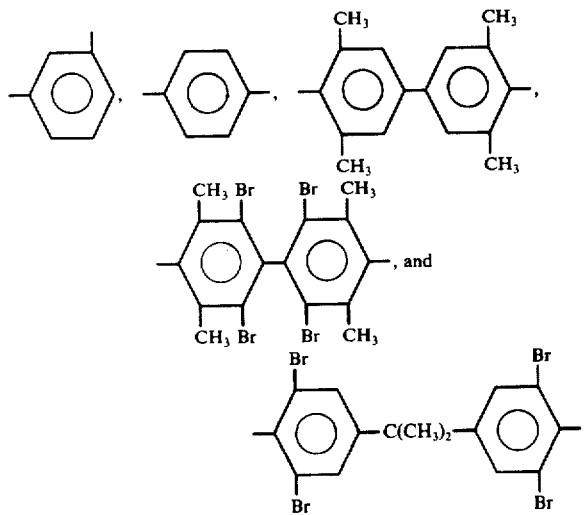

and (b) divalent organic radicals of the general formula

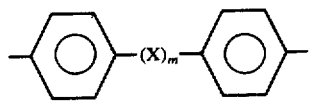

where X is a member selected from the class consisting of divalent radicals of the formulas

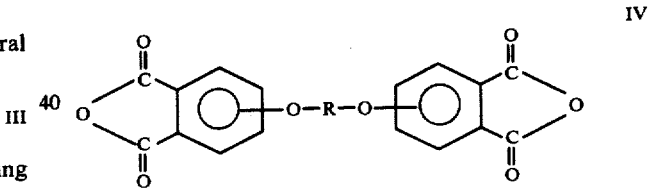

I

—O— , and —S— , where $m$ is 0 or 1, $y$ is a whole number from 1 to 5, and R' is the phenyl radical or an alkyl radical of from 1 to 2 carbon atoms, the said reaction being conducted in the presence of particulate potassium carbonate (hereinafter referred to as "carbonate") and a dipolar aprotic solvent selected from the class consisting of N,N-dimethyl acetamide, N,N-dimethyl formamide (DMF), N-methyl pyrrolidone, and mixtures of such solvents, and in the further presence of a particulate solid zeolite adsorbent.

Dianhydrides of the general formula

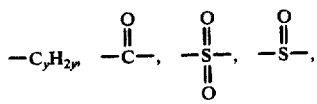          IV where R has the meanings given above have been used in the preparation of polymeric compositions by reacting the aforesaid dianhydrides with various organic diamines in the manner described in U.S. Pat. No. 3,847,867, issued Nov. 12, 1974, and assigned to the same assignee as the present invention which patent by reference is made part of the disclosures and teachings of the instant application. One of the important objectives in making these resins is to insure that the reactants required for such polymeric compositions are substantially pure and are made as economically as possible so that the resinous compositions prepared therefrom are obtained at the lowest possible cost.

One of the methods employed in the past for making the aforesaid aromatic bisimides of formula I comprises specifically forming a mixture of the dihydroxy compound, for instance bisphenol-A [(2,2-bis-4-hydroxyphenyl)propane], and sodium hydroxide in an aqueous medium with dimethyl sulfoxide (DMSO) and toluene. This mixture is heated to reflux to azeotropically remove water thereby producing an anhydrous dialkali metal salt. This salt is then reacted for a period of from 6 to 16 hours at about 60° C. with the nitrophthalimide of formula II to give the crude aromatic bisimide.

Thereafter, the crude aromatic bisimide has to be washed several times with water, treated with, for instance, methanol several times to remove the impurities and the solid material is then washed again to obtain an aromatic bisimide of the desired purity, which can then be processed in a manner described above to form the dianhydride of formula IV, which in turn can be reacted with the organic diamine in the manner described in the aforesaid U.S. Pat. No. 3,847,867.

We have now discovered, unexpectedly, that we are able to make the precursor aromatic bisimide of formula I more expeditiously and with fewer steps and by-products by effecting reaction between all the reactants at one time, under substantially anhydrous conditions, between a nitrophthalimide of formula II with an aromatic dihydroxy compound of formula III by employing a specific class of solvents, and additionally using potassium carbonate and a zeolite adsorbent. By means of our process, many of the steps and undesirable features of the previous method for making the bisimides of formula I are eliminated or obviated. Thus, whereas before dimethyl sulfoxide was necessary to help solubilize the dianion made from the aqueous sodium hydroxide and the dihydroxy aromatic compound and thus make its drying more complete, (incomplete drying greatly affected the purity of the bisimide produced), the concern about water is almost completely eliminated and strong unpleasant odors associated with the use of dimethyl sulfoxide (which was essential in the above-described process) are no longer a problem. Moreover, the refluxing with the aqueous base additionally made the use of dimethyl sulfoxide necessary, since most other dipolar aprotic solvents contained functionalities which reacted with the aqueous base. Furthermore, the dimethyl sulfoxide was difficult to recover since it could not be distilled at atmospheric pressure. Also, the necessity for azeotroping the formed water (which was time-consuming and expensive) before the addition of the nitrophthalimide, is substantially eliminated. Finally, in the past the dianion salt had to be cooled before adding the nitrophthalimide and then again heated for at least 6 hours to insure complete reaction; this step is also eliminated. By means of our invention, the preparation of the bisimide proceeds readily with a minimum of steps and when isolated is almost pure enough to be ready for use in the next step for hydrolysis and conversion of the dianhydride of formula IV.

We have also discovered that by employing the above combination of ingredients, additional improvements were derived. Specifically, the reaction between the nitrophthalimide and the dihydroxy aromatic compound led primarily to the bisimide product in good yields and ultimately with little if any contamination with such materials as ethers, or half-addition products, or amide acids of the formulas

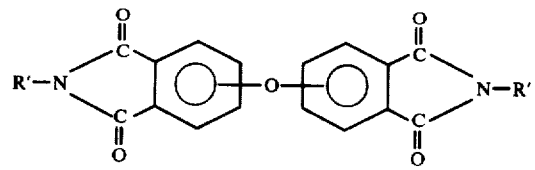

V

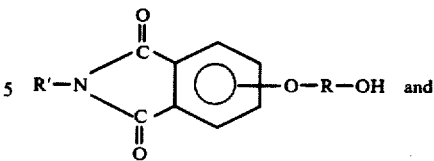

VI

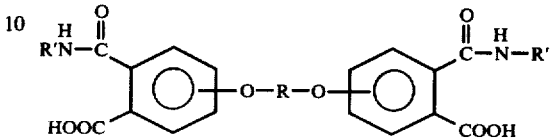

VII where R and R' have the meanings above. The presence of these contamination products in any significant amounts leads to reduced overall yield of the desired bisimide regardless of the manner by which the bisimide product is worked up including that of using methylene chloride liquid-liquid extractions more particularly disclosed and claimed in application Ser. No. 658,501 filed Feb. 17, 1976 in the names of Donald S. Johnson and Frank J. Williams, and assigned to the same assignee as the present invention. As a matter of fact, if such contamination products are present, hydrolysis of these products could lead to emulsion problems which would preclude the use of the above-described Johnson and Williams process for further purifying the bisimide, if this became necessary.

In the copending application of Donald S. Johnson and Howard M. Relles, Ser. No. 598,950 filed July 25, 1975, is disclosed and claimed a process for making aromatic tetracarboxylic acids by the reaction of a nitrophthalimide and an aromatic dihydroxy compound, such as bisphenol-A, using substantially anhydrous conditions and employing potassium carbonate as one of the reactants and dimethyl sulfoxide as the solvent medium in which the reaction is conducted. Although this invention gives the desired aromatic bisimide of formula I which can then be hydrolyzed to the required aromatic tetracarboxylic acid, the particular set of conditions and reactants also produces by-products, such as acid and amide-acid derivatives in large enough quantities to affect the yield of the more desired bisimide. Our process, by employing a specific class of aprotic solvents other than dimethyl sulfoxide, and using the molecular sieves, directs the course of the reaction to greater yields of the desired bisimide while at the same time minimizing and in some respects avoiding the formation of the undesirable by-products found in the aforesaid Johnson and Relles application.

It was surprising to find that when instead of using potassium carbonate, other carbonates such as sodium carbonate, lithium carbonate, magnesium carbonate and calcium carbonate unexpectedly gave lower yields of the desired aromatic bisimide and/or considerable quantities of undesirable by-products or unreacted reactants. Preferably, the potassium carbonate should be as anhydrous as possible. Generally any moisture which may be present should be that which is adsorbed on the carbonate and for best results should not exceed 5-10% adsorbed moisture based on the weight of the carbonate. To attain a substantially anhydrous condition may require subjecting the potassium carbonate to heating before introduction into the reaction environment. For best results the moisture should be less than 5%, by weight, based on the weight of the potassium carbonate.

Although both granular and powdery forms of the potassium carbonate can be employed in the practice of the present invention, the carbonate is preferred to be in the form of a powder of less than 50 microns average particle size, e.g., from 0.1 to 25 microns, as measured by scanning electron microscopy (SEM). Granular particles in excess of 50 microns, for example, having an average particle size of from 75 to 500 microns (when measured by SEM), can also be used, but generally it will be found that the reaction leading to the formation of the bisimide of formula I proceeds more readily when powdered carbonate is used and the by-product materials of formulas V, VI, and VII are present in smaller amounts and in some instances are completely eliminated.

The alumino-silicate zeolite adsorbents which may be used in the instant invention include the synthetic and natural zeolites, also known as molecular sieves. These zeolites are well known in the art and are detailed in the book entitled *Molecular Sieves,* Charles K. Hersh, Reinhold Publishing Company, New York (1961) which is incorporated herein by reference. Preferably, representative natural zeolites which may be employed in the instant invention include those in Table 3-1, on page 21, of the Hersh reference while representative molecular sieves include those in Table 5-1, on page 54, of the Hersh reference. Additional zeolite catalysts are set forth in *Organic Catalysts Over Crystalline Aluminosilicates,* P. B. Venuto and P. S. Landis, Advances in Catalysis, Vol. 18, pp 259 to 371 (1968), incorporated herein by reference.

A more complete description of the zeolites or molecular sieves may also be found in U.S. Pat. No. 3,840,610 issued Oct. 8, 1974. By reference, this patent, with all the descriptions of molecular sieves, is made part of the disclosures and teachings of the instant application, particularly as regards molecular sieves having different angstrom openings in the molecular sieve particulates.

The zeolite adsorbents are critical and perform an important function in the conduct of the present invention. Specifically, these compositions adsorb any water which is formed as a result of carrying out the reaction between the nitrophthalimide and the dihydroxy aromatic compound in the presence of the potassium carbonate. Unless essentially all the moisture formed is promptly removed by means of this adsorbent, hydrolytic side reactions can occur which would significantly interfere with the attainment of optimum yields of the desired bisimide. The amount and type of zeolite adsorbent used should be sufficient to take up essentially all the water which may be formed in the reaction. For this purpose it is possible to use zeolite adsorbents of different particle sizes and of a variety of pore openings.

Among the nitrophthalimides which may be employed are for instance 3-, and 4-nitro-N-methylphthalimide (the 4-nitro will hereinafter be referred to as "NPI"), 3- and 4-nitro-N-ethylphthalimide, and 3- and 4-nitro-N-phenylphthalimide.

In addition to the aromatic dihydroxy compounds which are obvious from a reading of formula III, other dihydric phenols which may be employed are, for instance, 2,2-bis-(2-hydroxyphenyl)propane;
2,4'-dihydroxydiphenylmethane;
bis-(2-hydroxyphenyl)-methane;
2,2-bis-(4-hydroxyphenyl)-propane (hereinafter identified as "bisphenol-A" or "BPA")
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide;
4,4'-dihydroxy diphenyl oxide; etc.

In carrying out the reaction, one should employ at least 2 mols of the phthalimide of formula II, and preferably from 2.1 to 4 or more mols of the latter per mol of the aromatic dihydroxy compound of formula III. We have found that a 5 to 10 mol percent excess of the phthalimide over that required to react with the aromatic dihydroxy compound, when combined with the molecular sieve, will usually give excellent yields of the desired bisimide.

The amount of potassium carbonate employed can be varied widely. Generally, we have found that at least 2 mols of the carbonate should be employed for each mol of the dihydric aromatic compound and preferably from about 2.05 to 3 mols of the former per mol of the dihydric aromatic compound are advantageously used.

The amount of aprotic solvent used is not critical and can also be varied widely, but enough of the latter solvent should be used in order to form a liquid medium for effecting the reaction. On a weight basis, we have found it convenient to use from about 1 to 20 parts or more of the selected aprotic solvent, per part of the total weight of the nitrophthalimide of formula II and the dihydric phenol of formula III.

We have found that although the above-described class of aprotic solvents can be employed alone in the practice of the invention, some improvement may be obtained if another inert solvent is employed with the aprotic solvent. Generally the solvent used will assist in obtaining a high enough boiling point (about 100 to 200° c.) whereby refluxing of the reactants in the presence of the carbonate can be effected. The cosolvent used with the aprotic solvent is any solvent which is inert to the reactants or to the resulting reaction mixture and should boil above 100° C. Among such cosolvents may be mentioned the isomeric xylenes, such as, m, o-, and p-xylene, toluene, chlorobenzene, bromobenzene, o-dichlorobenzene, anisole, ethylbenzene, mesitylene, octane, cycloheptane, diethyl and dimethyl ethers of ethylene glycol, etc. The inert cosolvent used should be generally liquid at room temperature, although this is not especially essential since it can also be a low melting solid which at reflux conditions or in the reaction mixture with the aprotic solvent forms a homogeneous solution. The cosolvent has an additional function of insolubilizing the potassium nitrite formed in the reaction and effectively removes the danger of the latter attacking the phthalimide ring and thus reducing the yield of desired bisimide of formula I.

The temperature at which reaction is carried out in the practice of our invention may be varied fairly widely. We have found that temperatures from 100° to 200° C. are advantageously used. If lower temperatures are employed, the reaction goes at a slower pace, while if too high a temperature is empolyed one is apt to find that damaging side reactions may cause a reduction in the yield of the desired bisimide. Atmospheric and superatmospheric pressures may be used.

The time of reaction may also be varied widely and only those times should be used which give optimum yields with a minimum of side reactions or loss of reactants or product. Generally we have found that the reaction goes to substantial completion within a period of from two to ten hours or more.

When a cosolvent is used with the aprotic solvent, the amount of inert cosolvent can be varied widely. Generally we have found that, just as in the case of using the aprotic solvent, the mixture of cosolvents should constitute on a weight basis of from 1 to 20 parts, or more of the total cosolvents per part of the reactants used. On a volume basis, the aprotic solvent and the inert cosolvent can vary quite widely, and can vary from about 10 to 90% of each of the solvents based on the total volume of the two solvents.

In all instances, substantially anhydrous conditions should be employed, and for best results an inert atmosphere should be employed such as conducting the reaction under a blanket of nitrogen. Stirring should be resorted to at all times in order to insure intimate contact of all the reactants and reagents required for optimum processing.

After the reaction is completed, the mixture can be diluted with methylene chloride which is a solvent for extracting the bisimide, and the methylene chloride solution can be washed several times with water and with an HCl solution of about 1 to 1.2 N HCl. The organic phase which will separate out is dried, for instance, with magnesium sulfate and concentrated by various means, such as under vacuum, to give a solid bisimide which is essentially pure at this stage. Thereafter, the bisimide can be processed in the manner described previously to make the aforementioned dianhydrides.

In addition to the advantages recited previously, our process offers several additional advantages over previous methods for making the bisimide from the reaction of a dihydric phenol and a nitrophthalimide employing an alkali-metal hydroxide in the form of the dianion of the dihydric phenol. In the past, the dianion salt formed from the reaction of the dihydric phenol and the alkali-metal hydroxide had to be kept under an inert atmosphere to avoid rapid air-oxidation and had to be completely anhydrous before it could be allowed to undergo the aromatic nitro-displacement reaction to form the bisimide compound. This required a long period of time, for instance, from three to four days using a complex step of azeotropic distillation with toluene. Even after most of the water had been removed, it was necessary to scavenge the remaining amounts of water with dehydrating agents. Furthermore, once the dianion salt had been dried, two equivalents of the nitrophthalimide were added and the displacement reaction was then allowed to proceed for another period of time ranging from about 6 to 24 hours with ultimate additional workup required of the reaction product to isolate the desired bis-imide.

Our nitro-displacement reaction is significantly simplified because we are able to generate substituted-phenoxide ions in situ with the carbonate in the presence of the nitrophthalimide, thus avoiding the need to prepare the dianion of the dihydric aromatic compound in advance. Although it was expected that imide-ring opening by the carbonate would compete with the nitro-displacement reaction, it was surprising to find that if the ring-opened compound was formed, it can apparently ring-close again under these conditions to regenerate the nitro-imide which can undergo displacement. It was also unexpected to find that there was little reaction between the carbonate and the dipolar aprotic solvents which contained amide functionalities. Thus, all the ingredients can be placed in the reaction vessel at the same time, which simplifies the procedure and eliminates the need for a later addition of the nitrophthalimide.

In order that those skilled in the art may better understand how the present invention may be practiced, the following examples are given by way of illustration and not by way of limitation. All reactions were conducted under a nitrogen atmosphere with stirring. The $K_2CO_3$ powder used had an average particle size of 0.1 to 1.0 micron when measured by SEM, while the granular $K_2CO_3$ had an average particle size when measured by SEM of about 500 microns.

The sieve used in the following example was Linde Molecular Sieves, Type 4A, manufactured by Union Carbide Corporation.

EXAMPLE 1

A mixture of 4.53 grams (0.022 mol) 4-nitro-N-methylphthalimide (NPI), 2.28 grams (0.01 mol) BPA, 3.32 grams (0.024 mol) powdered anhydrous potassium carbonate, 30 ml anhydrous DMF, 10 grams of 4A molecular sieve, and 0.54 gram hexamethylbenzene (used only to measure yield by proton nmr) was heated under a nitrogen atmosphere in an oil bath at 145° C. for 2 hours. After cooling to room temperature (about 25° C.), a 2 ml sample was removed from the rection mixture, diluted with 2 ml $CH_2Cl_2$, and filtered to remove the molecular sieve. The solution was washed three times with 2 ml 5% aqueous $NaHCO_3$, once with 2 ml of a 1.2N HCl solution to remove all traces of DMF, and once with $NaHCO_3$ to remove any trace of HCl. The organic phase was dried with magnesium sulfate and concentrated. Analysis by proton nmr and $^{13}C$ nmr showed a 97% yield of the desired bisphenol-A bisimide (BPA-BI) of the formula

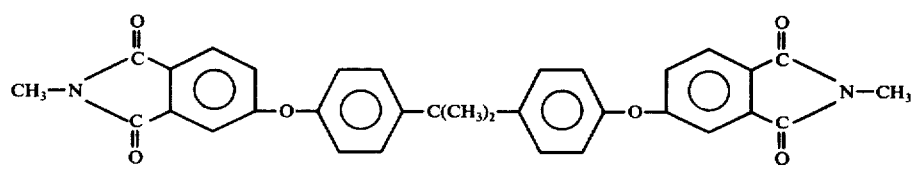

V with no evidence of unreacted BPA or the bisether and half-addition products, respectively, of the formulas

VI

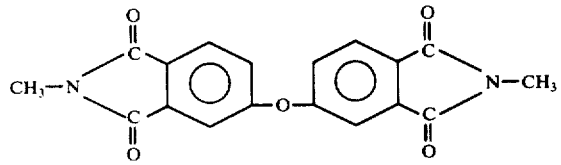

and

VII

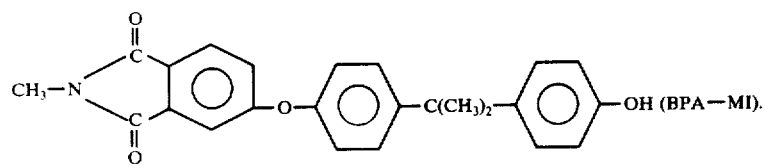

EXAMPLE 2

When Example 1 was repeated exactly except that the molecular sieve was omitted, the yield of the BPA-BI of formula V was down to 78% with 14% of the by-products being the BPA-MI of formula VII.

EXAMPLE 3

When Example 1 was repeated exactly except that the molecular sieve was omitted and 30 ml dimethyl sulfoxide was used in place of the DMF, the yield of BPA-BI of formula V was 39%, with 5% being the BPA-MI of formula VII. Most of the remaining product was the amide acids of the formula

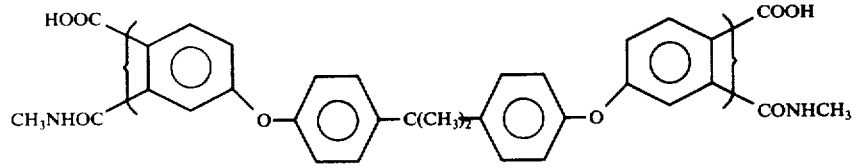

EXAMPLE 4

In this example the same conditions of reaction and reactants including the powdered potassium carbonate were employed as in Example 1 with the exception that the molar quantities of the NPI and the time of reaction were varied. The identity of the desired BPA-BI and by-products was established by the same means as in Example 1. The following Table 1 shows the results obtained as a result of the aforesaid conditions. Included in the table for comparison are the results of Example 1.

tion of the products obtained was made in the same manner as in Example 1. Table 2 shows the results of these tests with the results of Example 1 being found in this table for comparison purposes.

Table 2

|  | [a]Ex. 1 | [b]Test Number | | |
|---|---|---|---|---|
|  |  | 5 | 6 | 7 |
| Time of heating (hours) | 2 | 2 | 4 | 6 |
| % Yield BPA-BI - Formula V | 97 | 73 | 90 | 90 |
| % Yield BPA-MI - Formula VII | 0 | 21 | 5 | Trace |
| % Unreacted BPA | 0 | 3 | 0 | 0 |
| % Yield Diether - Formula VI | 0 | Small Quantity | 2.5 | 11 |

[a]Powdered $K_2CO_3$

[b]Granular $K_2CO_3$

EXAMPLE 6

In this example, powdered $Na_2CO_3$ and certain powdered carbonates such as lithium carbonate, magnesium carbonate, and calcium carbonate (each having an average particle size stated in the attached table), were employed in the same manner as in Example 1 using otherwise the identical reactants and conditions and concentrations of ingredients but varying the time of heating in one instance (for $Na_2CO_3$). For comparison, the test Table 1

|  |  | Test Number | | | |
|---|---|---|---|---|---|
|  | Ex. 1 | 1 | 2 | 3 | 4 |
| Time of heating (hours) | 2 | 2 | 2 | 4 | 6 |
| Molar % Excess of NPI over BPA | 10 | 5 | 0 | 0 | 0 |
| % Yield BPA-BI - Formula V | 97 | 97 | 90 | 93 | 88 |
| % Yield BPA-MI - Formula VII | 0 | Trace | 5 | Trace | 0 |
| % Unreacted BPA | 0 | 0 | 0 | 0 | 0 |
| % Yield Diether - Formula VI | 0 | 0 | 0 | 0 | 0 |

EXAMPLE 5

Employing the conditions and the same reactants as in Example 1 and using a 10 mol percent excess of NPI over the BPA, a comparison was made between using granular $K_2CO_3$ and powdered $K_2CO_3$. The identification results using the powdered potassium carbonate shown in Example 1 together with the powdered sodium carbonate are recited in the following Table 3 for comparison with the other carbonates described. All the carbonates were powdered and of essentially the same average particle size as the potassium carbonate.

Table 3

|  | Ex. 1 | [b]8 | [b]9 | [c]10 | [d]11 | [e]12 |
|---|---|---|---|---|---|---|
| Time of heating (hours) | 2 | 2 | 6.7 | 2 | 2 | 2 |
| %Yield BPA-BI - Formula V | 97 | 72 | 98 | 7 | 10 | 5 |
| % Yield BPA-MI - Formula VII | 0 | 22 | Trace | 28 | 28 | 14 |
| % Unreacted BPA | 0 | 2 | 0 | 56 | 58 | 76 |
| % Yield Diether - Formula VI | 0 | Slight Quantity | 9 | 0 | 0 | 0 |

[a]The NPI was in a 10 mol percent excess over the BPA
[b]Powdered $Na_2CO_3$ - average particle size from 2 to 25 microns
[c]Powdered $Li_2CO_3$ - average particle size from 2.5 to 25 microns
[d]Powdered $MgCO_3$ - average particle size less than 1 micron
[e]Powdered $CaCO_3$ - average particle size from 2.5 to 10 microns It was surprising to find that, for instance, lithium carbonate which is an alkali-metal carbonate similar to the potassium carbonate, acted so differently from the latter carbonate. Additionally, it was surprising to find that sodium carbonate acted so differently from potassium carbonate, thereby clearly establishing the unexpected and unobvious advantages and results by using potassium carbonate for purposes of the present invention.

EXAMPLE 7

In this example the same conditions and the same reactants were employed as in Example 1 using a 10 mol percent excess of the NPI, but instead of the BPA, 2.18 grams (0.01 mol) 4,4'-dihydroxy diphenyl sulfide was used. Similarly as was done in Example 1, the reactants with the powdered potassium carbonate and the 4A-molecular sieve were heated for two hours at the end of which time, as a result of proton nmr and $^{13}C$ nmr analyses, it was found that a 93% yield was obtained of the desired bisimide having the formula

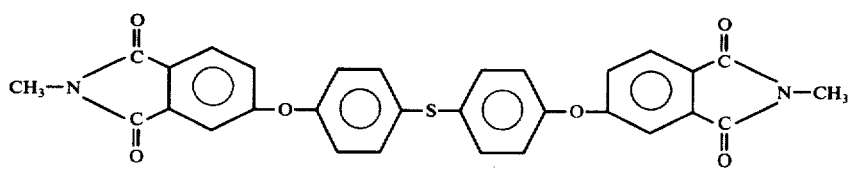

with 2% of the half-addition product having the formula

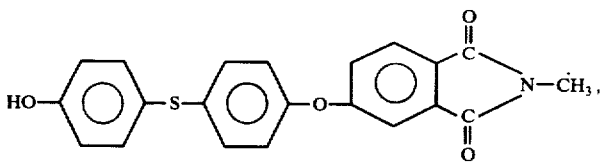

there being no evidence of either unreacted 4,4'-dihydroxy diphenyl sulfide or of the diether of formula VI.

EXAMPLE 8

Employing the same ingredients and conditions as described in Example 1, but substituting 1.10 gram (0.01 mol) of hydroquinone for the BPA, the mixture of ingredients was heated for two hours and thereafter the reaction product was isolated and its composition established by infrared and by analysis for carbon, hydrogen, and nitrogen as being the bisimide having the formula

X

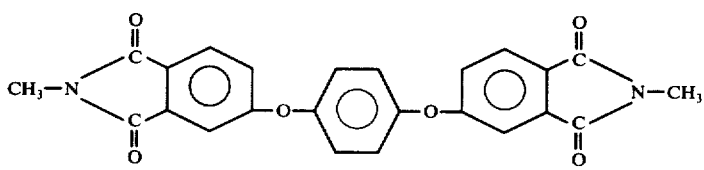

This compound had a melting point of 283°–285° C. Only 7% of the half-addition product of the formula

XI

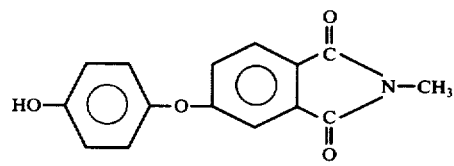

was found in the reaction product. The analyses for the compound of formula X were as follows:

VIII

|  | Found | Calculated |
|---|---|---|
| % C | 66.3 | 67.3 |
| % H | 3.9 | 3.7 |
| % N | 6.4 | 6.5 |

IX

It will of course be apparent to those skilled in the art that instead of using the nitrophthalimides of the foregoing examples, other nitrophthalimides, examples of which have been given above, can be employed in their place without departing from the scope of the invention. In addition, instead of employing the dihydric phenols, molecular sieve, and nitrophthalimide recited in the previous examples, other dihydric phenols, molecular sieves, and nitrophthalimides, many examples which have been recited previously, can be used in their place within the intended scope of the invention and with equivalent results. Finally, it will be apparent that the concentrations of ingredients and the conditions of reaction can also be varied widely as previously recited to obtain the desired aromatic bisimides expeditiously and usually in good yields.

As pointed out above, the aromatic bisimides obtained in accordance with the present invention may be hydrolyzed to the tetraacids and then dehydrated to form the dianhydrides which in turn can be reacted with various organic diamines such as meta-phenylene diamine, 4,4'-diaminodiphenylmethane, 4,4'-diaminodiphenyl oxide, benzidine, 4,4'-diaminodiphenyl-sulfone, 3,3'-dimethylbenzidine, etc., to yield resinous compositions which because of their desirable heat resistance can be employed in applications where elevated temperatures may be encountered. Thus, these polymeric compositions, whether filled or unfilled, can be employed in applications requiring good mechanical, electrical and heat resistance properties. They are eminently suitable for use in the manufacture of insulators, transformer blocks, motor armatures, printed circuits, honeycomb structure panels and compressor vanes, etc. In the form of solutions with suitable solvents, they can be used to coat electrical conductors such as copper or aluminum wire and the resinous materials so deposited can be heat-treated to effect conversion to the final polymerized state.

What we claim as new and desire to secure by Letters Patent is:

1. The process for making aromatic imides of the general formula

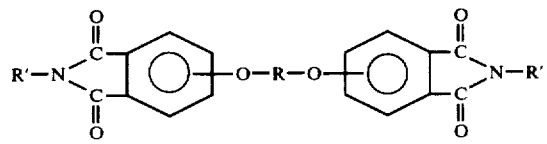

which comprises (1) simultaneously effecting reaction under substantially anhydrous conditions between a nitrophthalimide of the general formula

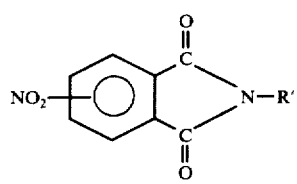

with a dihydroxy compound of the general formula

HO-R-OH where R is a member selected from the class consisting of a. divalent radicals of the formula

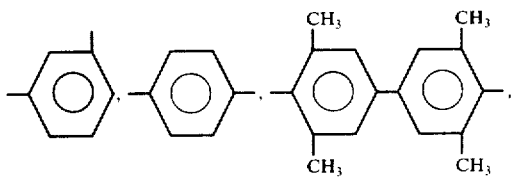

and (b) divalent organic radicals of the general formula where X is a member selected from the class consisting of divalent radicals of the formulas $-C_yH_{2y}-$, $-\overset{O}{\underset{\parallel}{C}}-$, $-\overset{O}{\underset{\underset{\parallel}{O}}{\overset{\parallel}{S}}}-$, $-\overset{O}{\underset{\parallel}{S}}-$, —O— and —X—, where $m$ is 0 or 1, $y$ is a whole number from 1 to 5, and R' is a phenyl radical or an alkyl radical of from 1 to 2 carbon atoms, the said reaction being conducted in a solvent selected from the class consisting of N,N-dimethyl formamide, N,N-dimethyl acetamide, N-methylpyrrolidone, and mixtures of such solvents and in the further presence of a particulate potassium carbonate and a molecular sieve zeolite adsorbent, and (2) isolating the formed aromatic bisimide.

2. The process as in claim 1 wherein the nitrophthalimide is 4-nitro-N-methylphthalimide.

3. The process as in claim 1 wherein the dihydroxy compound is bisphenol-A.

4. The process as in claim 1 wherein the potassium carbonate has an average particle size below 50 microns.

5. The process as in claim 1 wherein the solvent is dimethyl formamide.

6. The process for making a bisimide having the formula

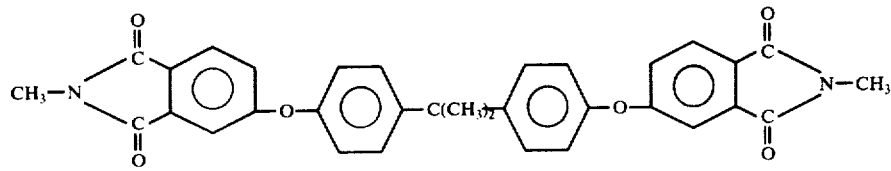

which comprises (1) effecting reaction between 4-nitro-N-methylphthalimide and bisphenol-A in the presence of particulate potassium carbonate, dimethyl formamide as the solvent, and a molecular sieve zeolite adsorbent, and (2) isolating the formed bisimide.

7. The process as in claim 6 wherein the $K_2CO_3$ has an average particle size of less than 50 microns.

8. The process as in claim 1 wherein at least 2 mols of the potassium carbonate are employed per mol of the dihydroxy aromatic compound.

9. The process as in claim 1 wherein the dihydroxy compound is hydroquinone.

10. The process as in claim 1 wherein the dihydroxy compound is bisphenol-A, the nitrophthalimide is 4-nitro-N-methylphthalimide, and the $K_2CO_3$ has an average particle size of from 0.1 to 1 micron.

11. The process as in claim 1 wherein the dihydroxy compound is 4,4'-dihydroxy diphenyl sulfide.

* * * * *